United States Patent
Nerem et al.

(10) Patent No.: US 12,409,212 B2
(45) Date of Patent: Sep. 9, 2025

(54) IMMUNOGENIC GEL COMPOSITIONS

(71) Applicant: BOEHRINGER INGELHEIM VETMEDICA GMBH, Ingelheim am Rhein (DE)

(72) Inventors: Joel Lee Nerem, Edgerton, MN (US); Daniel Brian Hanson, Edgerton, MN (US); Fernando Lopes Leivas Leite, Atlanta, GA (US); Justin Howard Rustvold, Dacula, GA (US); Amanda Marie Sponheim, Osage, IA (US)

( * ) Notice: Subject to any disclaimer, the term of this patent is extended or adjusted under 35 U.S.C. 154(b) by 0 days.

(21) Appl. No.: 18/050,577

(22) Filed: Oct. 28, 2022

(65) Prior Publication Data

US 2023/0141226 A1   May 11, 2023

Related U.S. Application Data

(60) Provisional application No. 63/266,984, filed on Jan. 21, 2022, provisional application No. 63/264,615, filed on Nov. 29, 2021, provisional application No. 63/263,360, filed on Nov. 1, 2021.

(51) Int. Cl.
| | |
|---|---|
| *A61K 39/02* | (2006.01) |
| *A61K 9/00* | (2006.01) |
| *A61K 9/06* | (2006.01) |
| *A61K 39/112* | (2006.01) |
| *A61P 31/04* | (2006.01) |
| *A61K 39/00* | (2006.01) |

(52) U.S. Cl.
CPC ........ *A61K 39/0275* (2013.01); *A61K 9/0053* (2013.01); *A61K 9/06* (2013.01); *A61K 39/0208* (2013.01); *A61P 31/04* (2018.01); *A61K 2039/522* (2013.01); *A61K 2039/542* (2013.01); *A61K 2039/545* (2013.01); *A61K 2039/552* (2013.01)

(58) Field of Classification Search
None
See application file for complete search history.

(56) References Cited

U.S. PATENT DOCUMENTS

| | | | |
|---|---|---|---|
| 4,253,822 A | 3/1981 | Marsh | |
| 2015/0351428 A1* | 12/2015 | Izard | A23K 20/184 424/234.1 |
| 2019/0000763 A1* | 1/2019 | Pilgaonkar | A61K 9/4808 |

FOREIGN PATENT DOCUMENTS

| | | | |
|---|---|---|---|
| CN | 108926710 A | 12/2018 | |
| DE | 2843295 A1 | 10/1980 | |
| JP | 2001008640 A | 1/2001 | |
| JP | 2006528882 A | 12/2006 | |
| JP | 2008545618 A | 12/2008 | |
| WO | 2005011731 A1 | 2/2005 | |
| WO | WO-2006099561 A1 * | 9/2006 | ............. A61K 39/00 |
| WO | 2015187947 A1 | 12/2015 | |
| WO | 2023073640 A1 | 5/2023 | |

OTHER PUBLICATIONS

Help pigs through weaning challenges. All About Feed. https://www.allaboutfeed.net/animal-feed/feed-additives/help-pigs-through-weaning-challenges/ Mar. 23, 2015.*
Kumari et al. Polim Med. 2019; 49(2):71-79.*
Dictionary definition of "mat" https://www.dictionary.com/browse/mat retrieved Feb. 17, 2025.*
Roof, Michael B., "Vaccinating for ileitis", Allen D. Leman Swine Conference, 2001, pp. 121-126.
Collins, Alison M., "Advances in Ileitis Control, Diagnosis, Epidemiology and the Economic Impacts of Disease in Commercial Pig Herds", Agriculture, vol. 3, 2013, pp. 536-555.
Nogueira, Mariana G., "Immunity to Lawsonia intracellularis vaccination in pigs". The University of Sydney, 2013, pp. 2-162.
McOrist et al., "Antigenic Analysis of Campylobacter Species and an Intracellular Campylobacter-Like Organism Associated with Porcine Proliferative Enteropathies", Infection and Immunity, vol. 57, No. 3, Mar. 1989, pp. 957-962.
Nogueira et al., "Immunological responses to vaccination following experimental Lawsonia intracellularis virulent challenge in pigs", Veterinary Microbiology, vol. 164, 2013, pp. 131-138.
Dale et al., "Vaccination Against Proliferative Enteropathy in Pigs", Manipulating Pig Production VI, 1997, pp. 182.
Kroll et al., "Proliferative enteropathy: a global enteric disease of pigs caused by Lawsonia intracellularis", Animal Health Research Reviews, vol. 6, No. 2, 2005, pp. 173-197.
Anonymous, "Underline Gel Concentrate Improves Oral Swine Erysipelas Vaccination", Jul. 6, 2017 (Jul. 6, 2017), XP93018159, Retrieved from the Internet: URL:https://web.archive.org/web/20170706150356/https://www.asp-inc.com/underline-international/.
Abstract in English for DE2843295A1.
Abstract in English for JP2001008640A.
Written Opinion for PCT/IB2022/060403.

* cited by examiner

*Primary Examiner* — Oluwatosin A Ogunbiyi
(74) *Attorney, Agent, or Firm* — Steffan Finnegan

(57) ABSTRACT

Prodn. of stable, highly immunogenic bacterial mutants for live vaccines from wild types or highly immunogenic strains with one marker (which are attenuated by other causes such that multiplication is not limited). The process comprises selecting stable clones with the non-multiplication-limiting attenuating marker of purine-degendence. The process esp. applies to *Salmonella* vaccines.

23 Claims, No Drawings

IMMUNOGENIC GEL COMPOSITIONS

BACKGROUND

*Lawsonia* (*L.*) *intracellularis*, the causative agent of porcine proliferative enteropathy ("PPE"), affects virtually all animals, including: rabbits, ferrets, hamsters, foxes, horses, and other animals as diverse as ostriches and emus. *L. intracellularis* is globally the most prevalent enteric pathogen in swine and is causing significant losses in swine production across the globe.

*L. intracellularis* vaccines have been approved for use in the United States and Europe (trademark Enterisol®Ileitis) which are based on live attenuated *L. intracellularis* isolates described in WO96/39629 A1 and WO2005/011731 A1.

Killed *L. intracellularis* vaccines have been described as well, such as in WO2009144088 A2, WO97/20050 A1 and WO2002/26250 A2.

*Salmonella enterica* subsp. *enterica* serovar *Choleraesuis* (SC) and *Salmonella enterica* subsp. *enterica* serovar *Typhimurium* (ST) have been identified as primary pathogens in swine. ST is a primary cause of enteritis and subclinical production losses in growing or finishing pigs and contributes to environmental and carcass contamination. Due to the zoonotic potential, interventional programs for ST have been established across the world attempting to reduce carcass contamination with the ultimate goal of reducing human *salmonellosis* cases.

*Salmonella* infections have traditionally been treated using SC vaccines, for example, ENTERISOL SC-54® *Salmonella Choleraesuis* Vaccine Avirulent Live Culture (Boehringer Ingelheim). This product is described in U.S. Pat. Nos. 5,436,001 and 5,580,557, both incorporated by reference herein.

*Salmonella Typhimurium* isolates include a *Salmonella Typhimurium* 421/125 of Impfstoffwerk Dessau-Tomau (IDT), Germany. This isolate is used as an active ingredient of SALMOPORC, a live *Salmonella* vaccine, marketed by Ceva (Ceva Santé Animale). The preferred ST of the invention is described by DE2843295 and its equivalent U.S. Pat. No. 3,856,935, both incorporated by reference herein.

Further, there is a live *Salmonella Choleraesuis-Typhimurium* vaccine (Enterisol® *Salmonella* T/C) which comprises both *Salmonella Choleraesuis* and *Salmonella Typhimurium*.

Both, the live *Lawsonia intracellularis* vaccines (such as Enterisol®Ileitis) and the live *Salmonella* vaccines (such as ENTERISOL SC-54®) are given orally by oral drench or by the drinking water.

However, the traditional oral drench administration needs individual pig handling, which is labor expensive and is stressful to the pig.

Using the administration by the drinking water, piglets that are not yet drinking water are not vaccinated and vaccination via drinking water is not possible prior to weaning. Further, the administration by the drinking water involves many steps.

However, in general, early vaccination is needed for efficiently protecting the animals. In regard to bacterial live vaccines, antibiotics may interfere with the efficacy of said bacterial live vaccine. Therefore, it would be beneficial to vaccinate animals as soon as possible after birth, to vaccinate animals in the medication free window (vaccination at a time most pigs aren't receiving antimicrobials) during the suckling period.

Further, the U.S. pork industry is suffering from a serious labor shortage, negatively impacting farms and processing plants (see https://nppc.org/issues/issue/agriculture-labor-issues/).

Therefore, there is a need for earlier and more efficient vaccination methods with reduced individual animal handling, reduced labor and reduced stress for the animals.

DESCRIPTION OF THE INVENTION

Before the aspects of the present invention are described, it must be noted that as used herein and in the appended claims, the singular forms "a", "an", and "the" include plural reference unless the context clearly dictates otherwise. Thus, for example, reference to "an antigen" includes a plurality of antigens, reference to the "virus" is a reference to one or more viruses and equivalents thereof known to those skilled in the art, and so forth. Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications mentioned herein are incorporated herein by reference for the purpose of describing and disclosing the cell lines, vectors, and methodologies as reported in the publications which might be used in connection with the invention. Nothing herein is to be construed as an admission that the invention is not entitled to antedate such disclosure by virtue of prior invention.

The present invention solves the problems inherent in the prior art and provides a distinct advance in the state of the art. Generally, the present invention provides an immunogenic gel composition comprising a *Lawsonia intracellularis* antigen and/or a *Salmonella* spp. antigen and a gel composition suitable for oral administration.

Advantageously, the experimental data provided herein disclose that the animals consumed the vaccine gel compositions. The uptake of the live *Lawsonia intracellularis* and *Salmonella* gel vaccine was even superior compared to the conventional oral drench application. Further, the vaccine gel compositions were as efficient as the conventional application methods.

However, advantageously, animals were vaccinated earlier in time, within the medication free window (during the suckling period), with none or reduced individual pig handling and reduced stress for the animals.

The term "gel" is well known to a person skilled in the art. Further, the term "gel" is further defined below. Furthermore, suitable gels are known by the person skilled in the art and are commercially available, such as the Underline® gel (Animal Science Products, Nacogdoches, TX).

The term "immunogenic composition" refers to a composition that comprises at least one antigen, which elicits an immunological response in the host to which the immunogenic composition is administered. Such immunological response may be a cellular and/or antibody-mediated immune response to the immunogenic composition of the invention. Preferably, the immunogenic composition induces an immune response and, more preferably, confers protective immunity against one or more of the clinical signs of an animal pathogen infection. The host is also described as an "animal".

Usually, an "immunological response" includes but is not limited to one or more of the following effects: the production or activation of antibodies, B cells, helper T cells, suppressor T cells, and/or cytotoxic T cells and/or gamma-delta T cells, directed specifically to an antigen or antigens included in the immunogenic composition of the invention. Preferably, the host will display either a protective immunological response or a therapeutically response.

A "protective immunological response" or "protective immunity" will be demonstrated by either a reduction or lack of clinical signs normally displayed by an infected host, a quicker recovery time and/or a lowered duration of infectivity or lowered pathogen titer in the tissues or body fluids or excretions of the infected host.

In case where the host displays a protective immunological response such that resistance to new infection will be enhanced and/or the clinical severity of the disease reduced, the immunogenic composition is described as a "vaccine".

An "antigen" as used herein refers to, but is not limited to, components which elicit an immunological response in a host to an immunogenic composition or vaccine of interest comprising such antigen or an immunologically active component thereof. The antigen or immunologically active component may be a whole microorganism (in inactivated or modified live form), or any fragment or fraction thereof, which, if administered to a host, can elicit an immunological response in the host. The antigen may be or may comprise complete live organisms in either its original form or as attenuated organisms in a so called modified live vaccine (MLV). The antigen may further comprise appropriate elements of said organisms (subunit vaccines) whereby these elements are generated either by destroying the whole organism or the growth cultures of such organisms and subsequent purification steps yielding in the desired structure(s), or by synthetic processes induced by an appropriate manipulation of a suitable system like, but not restricted to bacteria, insects, mammalian or other species, and optionally by subsequent isolation and purification procedures, or by induction of said synthetic processes in the animal needing a vaccine by direct incorporation of genetic material using suitable pharmaceutical compositions (polynucleotide vaccination). The antigen may comprise whole organisms inactivated by appropriate methods in a so called killed vaccine (KV). If the organism is a bacterium, the killed vaccine is called a bacterin.

In one aspect of the present invention the immunogenic gel composition comprises a *Lawsonia intracellularis* antigen and a gel composition suitable for oral administration.

In one aspect of the present invention the immunogenic gel composition comprises a *Salmonella* spp. antigen and a gel composition suitable for oral administration.

In one aspect of the present invention the immunogenic gel composition comprises a *Lawsonia intracellularis* antigen and a *Salmonella* spp. antigen and a gel composition suitable for oral administration.

Advantageously, the experimental data provided herein show that the *Lawsonia intracellularis* antigen and the *Salmonella* antigen can be combined when administered in a gel composition (no interreference was observed).

In one aspect of the present invention the *Lawsonia intracellularis* antigen and/or the *Salmonella* spp. antigen are whole cell bacteria.

Lawsonia Antigen

The term "*Lawsonia intracellularis*" is known by the person skilled in the art. *Lawsonia intracellularis* is the causative agent of porcine proliferative enteropathy ("PPE").

In one aspect of the present invention the *Lawsonia intracellularis* antigen is killed *Lawsonia intracellularis* or modified live *Lawsonia intracellularis*.

In one aspect of the present invention the killed *Lawsonia intracellularis* is a whole cell killed *Lawsonia intracellularis*.

Killed *L. intracellularis* vaccines have been described in WO2009144088 A2, WO97/20050 A1 and WO2002/26250 A2.

Any conventional inactivation method can be used for purposes of the present invention. Thus, inactivation can be performed by chemical and/or physical treatments which are known to the person skilled in the art. Preferred inactivation methods include the addition of cyclized binary ethylenimine (BEI) including the addition of a solution of 2-bromoethyleneamine hydrobromide (BEA), which has been cyclized to binary ethylenimine (BEI). Preferred further chemical inactivation agents comprise but are not limited to Triton X-100, Sodium deoxycholate, Cetyltrimethylammonium bromide, β-Propiolactone, Thimerosal, Phenol and Formaldehyde (Formalin). However, the inactivation may also comprise a neutralization step. Preferred neutralization agents include but are not limited to sodium thiosulfate, sodium bisulfite and the alike.

Preferred formalin inactivation conditions include formalin concentration between from about 0.02% (v/v)-2,0% (v/v), more preferably from about 0.1% (v/v)-1,0% (v/v), still more preferably from about 0.15% (v/v)-0.8% (v/v), even more preferably from about 0.16% (v/v)-0.6% (v/v), and most preferably about 0.2% (v/v)-0.4% (v/v). Incubation time depends on the resistance of the pathogen. In general, the inactivation process is performed until no growth of the pathogen can be detected in a suitable cultivation system.

Preferably, the inactivated *Lawsonia intracellularis* are formalin inactivated, preferably using the concentrations as described hereinabove.

Preferred β-Propiolactone inactivation conditions include β-Propiolactone concentration between from about 0,005% (v/v)-4,0% (v/v) and more preferably from about 0.05% (v/v)-2,0% (v/v). Incubation time depends on the resistance of the pathogen. In general, the inactivation process is performed until no growth of the pathogen can be detected in a suitable cultivation system.

Preferably, the inactivated *Lawsonia intracellularis* are inactivated by (3-Propiolactone, preferably using the concentrations as described hereinabove.

Preferably, the immunogenic composition comprises $10^2$ to $10^{14}$ cells killed *Lawsonia intracellularis* per dose, more preferably 104 to $10^{12}$ cells killed *Lawsonia intracellularis* per dose and even more preferably $10^6$ to $10^{10}$ cells killed *Lawsonia intracellularis* per dose.

Preferably, the immunogenic composition comprises an amount of 25 to 2000 µg killed *Lawsonia intracellularis* per dose, more preferably an amount of 50 to 1000 µg killed *Lawsonia intracellularis* per dose and even more preferably an amount of 100 to 800 µg killed *Lawsonia intracellularis* per dose.

In one aspect of the present invention the immunogenic gel composition comprises $10^6$ to $10^{10}$ cells killed *Lawsonia intracellularis* per dose or an amount of 100 to 800 µg killed *Lawsonia intracellularis* per dose.

In one aspect of the present invention the *Lawsonia intracellularis* antigen is modified live *Lawsonia intracellularis*.

In one aspect of the present invention the *Lawsonia intracellularis* antigen is an avirulent isolate of *Lawsonia intracellularis* or an attenuated *Lawsonia intracellularis*.

The term "attenuated" refers to a pathogen having a reduced virulence. In the present invention "attenuation" is synonymous with "avirulent" or "modified live". In the present invention, an attenuated animal pathogen (such as *Lawsonia intracellularis* or *Salmonella* spp.) is one in which the virulence has been reduced so that it does not cause clinical signs of an animal pathogen infection (such as *Lawsonia intracellularis* or *Salmonella* spp.) but is capable of inducing an immune response in the target animal, but may also mean that the clinical signs are reduced in incidence or severity in animals infected with the attenuated animal pathogen in comparison with a "control group" of animals infected with non-attenuated animal pathogen and not receiving the attenuated bacteria. In this context, the term "reduce/reduced" means a reduction of at least 10%, preferably 25%, even more preferably 50%, still more preferably 60%, even more preferably 70%, still more preferably 80%, still more preferably 90%, even more preferably 95% and most preferably of 100% as compared to the control group as defined above. Thus, an attenuated, avirulent animal pathogen strain or isolate is one that is suitable for incorporation into an immunogenic composition comprising a modified live animal pathogen.

Pathogenic and non-pathogenic attenuated bacteria strains of *L. intracellularis* are well known in state of the art. For example, WO 96/39629 and WO 05/011731 describe non-pathogenic attenuated strains of *L. intracellularis* and methods for the preparation thereof.

In particular, WO 96/39629 describes the preparation of attenuated bacteria strains of *L. intracellularis* and the deposited strain ATCC 55783.

WO 05/011731 describes the preparation of attenuated bacteria strains of *L. intracellularis* and the deposited strain PTA-4926.

In one aspect of the present invention the avirulent isolate is PTA-4926 or ATCC 55783.

In one aspect of the present invention the *Lawsonia intracellularis* antigen or the avirulent *Lawsonia intracellularis* isolate or the attenuated *Lawsonia intracellularis* is the antigen or isolate in Enterisol®Ileitis. In general, Enterisol®Ileitis is administered to pigs of three weeks of age or older.

The recommended dose to be administered to the susceptible animal is preferably about 3.0 $TCID_{50}$ (tissue culture infective dose 50% end point)/dose to about 9.0 TCID50/dose and more preferably about 4.0 TCID50/dose to about 7.0 TCID50/dose.

In one aspect of the present invention the immunogenic gel composition comprises about 3.0 to about 9.0 $TCID_{50}$ of the modified live *Lawsonia intracellularis* per dose.

In one aspect of the present invention the immunogenic gel composition comprises about 4.0 to about 7.0 $TCID_{50}$ of the modified live *Lawsonia intracellularis* per dose.

The term "per dose" as used herein means that this is the dose per animal. However, the immunogenic gel composition comprises several doses if the immunogenic gel composition is for the administration of several animals in the barn or housing environment. Therefore, if in a barn are for example 10 animals to be vaccinated, the immunogenic composition will have to comprise 10 doses. Preferably, the immunogenic gel composition will even have a higher number of doses such as 11, 12, or 15 or 20 doses to make sure that every animal will receive an appropriate dose.

*Salmonella* Antigen

The term "*Salmonella* spp." is known by the person skilled in the art. *Salmonella Choleraesuis* (SC) and *Salmonella enterica* ser *Typhimurium* (ST) have been identified as a primary cause of enteritis and subclinical production losses in in growing or finishing pigs. Clinical *salmonellosis* in swine can be broadly separated into septicemia caused by *S. Choleraesuis* and enterocolitis associated with *S. Typhimurium*.

In one aspect of the present invention the *Salmonella* spp. antigen is killed *Salmonella* spp. or modified live *Salmonella* spp.

In one aspect of the present invention said *Salmonella* spp. is *Salmonella Choleraesuis* and/or *Salmonella Typhimurium*.

In one aspect of the present invention said *Salmonella* spp. is *Salmonella enterica* subsp. *enterica* serovar *Choleraesuis* and/or *Salmonella enterica* subsp. *enterica* serovar *Typhimurium*.

In one aspect of the present invention the killed *Salmonella* spp. is a whole cell killed *Salmonella* spp.

Conventional inactivation methods have been defined above.

In one aspect of the present invention the *Salmonella* spp. is a whole cell killed *Salmonella* spp.

In one aspect of the present invention the immunogenic gel composition comprises $10^6$ to $10^{10}$ cells killed *Salmonella* spp. per dose or an amount of 100 to 800 µg killed *Salmonella* spp. per dose.

In one aspect of the present invention the *Salmonella* spp. antigen is modified live *Salmonella* spp.

In one aspect of the present invention the *Salmonella* spp. antigen is an avirulent isolate of *Salmonella* spp. or an attenuated *Salmonella* spp.

The term "attenuated" has been defined above.

Non-pathogenic attenuated bacteria strains of *Salmonella Choleraesuis* and *Salmonella Typhimurium* are well known in the state of the art.

*Salmonella Choleraesuis* strains have been described in U.S. Pat. Nos. 5,436,001 and 5,580,557. Further, an Avirulent Live Culture of *Salmonella Choleraesuis* (ENTERISOL SC-54®, Boehringer Ingelheim Vetmedica, Inc.) is commercially available.

*Salmonella Typhimurium* isolates include a *Salmonella Typhimurium* 421/125 of Impfstoffwerk Dessau-Tornau (IDT), Germany. This isolate is used as an active ingredient of SALMOPORC, a live *Salmonella* vaccine, marketed by IDT Biologika GmbH in Europe. The preferred ST of the invention is described by DE2843295 and its equivalent U.S. Pat. No. 3,856,935, both incorporated by reference.

Further, there is a live *Salmonella Choleraesuis-Typhimurium* vaccine (Enterisol® *Salmonella* T/C) commercially available which comprises both *Salmonella Choleraesuis* and *Salmonella Typhimurium*.

In one aspect of the present invention the *Salmonella* spp. antigen or the avirulent *Salmonella Choleraesuis* and/or *Salmonella Typhimurium* isolate is the antigen or isolate in ENTERISOL SC-54® and/or SALMOPORC and/or Enterisol® *Salmonella* T/C.

In one aspect of the present invention the immunogenic gel composition comprises about $1\times10^3$ to about $1\times10^{12}$ CFU of the *Salmonella* spp. per dose.

In one aspect of the present invention the immunogenic gel composition comprises about $1\times10^5$ to about $1\times10^{10}$ CFU of the *Salmonella* spp. per dose.

Gel Composition

In one aspect of the present invention the gel composition is viscous.

In some aspects of the invention, the gel composition has a viscosity of at least about 10, 20, 30, 40, 50, 60, 70, 80, 90, 100, 150, 200, 250, 300, 350, 400, 450, 500, 550, 600, 650, 700, 750, 800 cPs (mPa·s) or higher.

In one aspect of the present invention the gel composition has a viscosity of at least 150 mPa·s (at least 150 cP).

In one aspect of the present invention the gel composition has a viscosity of at least 100 mPa·s (at least 100 cP).

In one aspect of the present invention the gel composition has a viscosity of at least 50 mPa·s or at least 50 cP. In another aspect of the present invention the gel composition has a viscosity between 50 cP (50 mPa·s) and 150 cP (150 mPa·s). In yet another aspect of the present invention the gel composition has a viscosity between 50 cP (50 mPa·s) and 350 cP (350 mPa·s).

In one aspect of the present invention the gel composition has a viscosity of at least 25 mPa·s or at least 25 cP. In another aspect of the present invention the gel composition has a viscosity between 25 cP (25 mPa·s) and 150 cP (150 mPa·s). In yet another aspect of the present invention the gel composition has a viscosity between 25 cP (25 mPa·s) and 350 cP (350 mPa·s).

The measurement unit of viscosity is Pa·s (pascal second) or mPa·s (millipascal second). The conventional measurement unit is cP (centipoise). A centipoise is one millipascal-second (1 cP=$10^{-3}$ Pa·s=1 mPa·s).

In one aspect of the present invention gel composition comprises water and/or an adhesion enhancing agent and/or a pH adjusting agent and/or a stabilizer.

In some aspects of the invention, the compositions comprising an adhesion enhancing agent are viscous.

In one aspect the adhesion enhancing agent is polyvinyl pyrrolidone. In other aspects the adhesion enhancing agent is a hydrophilic polymer or copolymer that is linear or branched, crosslinked, is not biodegradable, or is selected from the group consisting of xanthan, guar, pectins, gums, guar derivatives, chitosan, dextran, maltodextrin, carrageenans, starch, polyethylene glycol, albumin, cellulose ethers, hyaluronic acid, carbaxymethylhydroxyethylcellulose, hydroxypropyl cellulose, gelatins, vinyl acetates, polyvinyl pyrrolidone-vinyl acetate copolymers, polyvinyl alcohols, polyphosphoesters, N-(2-hydroxyptopyl) methacrylamide (HPMA) copolymers, polyacrylic acids, polyacrylamides, polyoxazolines, divinyl ether-maleic anhydride, polyphosphazenes, including derivatives and substitutions and salts of any of the foregoing, and combinations thereof. In another aspect, the adhesion enhancing agent is a cellulose that includes one or more of hydroxypropylmethyl cellulose (HPMC), hydroxypropyl cellulose (HPC), hydroxyethyl cellulose (HEC), and carboxy methyl cellulose (CMC), and salts thereof.

In some aspects, the adhesion enhancing agent is in a final concentration (w/v) of about 0.1%, 0.2%, 03%, 0.4%, 0.5%, 0.6%, 0.7%, 0.8%, 0.9%, 1.0%, 1.1%, 1.2%, 1.3%, 1.4%, 1.5%, 1.6%, 1.7%, 1.8%, 1.9%, 2%, 3%, 4%, 5%, 6%, 7%, 8%, 9%, 1%, %11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, or 49%, or any ranges therebetween including, for example, from about 0.5% to 15% w/v, from about 0.5% to 10% w/v, from about 0.5% to 5% w/v, from about 0.5% to 2% w/v.

In one aspect, the adhesion enhancing agent is in a final concentration (w/v) of about 0.5% to 15% w/v In some aspects, the adhesion enhancing agent is a hydrophilic polymer or copolymer that is linear or branched, crosslinked, and/or is not biodegradable. Suitable adhesion enhancing agents include polyvinylpyrrolidone, polyvinylpyrrolidone vinyl acetate copolymers, waxes, mineral oil, plastigel (a blend of mineral oil and polyethylene), petrolatum, white petrolatum, shellac, versagel (blend of liquid paraffin, butene ethylene/styrene hydrogenated copolymer), polyethylene waxes, microcrystalline waxes, polyisobutene, polyvinylpyrrolidone vinyl acetate copolymers, and insoluble polyacrylate copolymers, xanthan, guar, pectins, gums, guar derivatives, chitosan, dextran, maltodextrin, carrageenans, starch, polyethylene glycol, albumin, cellulose ethers, hyaluronic acid, carbaxymethylhydroxyethylcellulose, hydroxypropyl cellulose, gelatins, vinyl acetates, polyvinyl pyrrolidone-vinyl acetate copolymers, polyvinyl alcohols, polyphosphoesters, N-(2-hydroxypropyl) methacrylamide (HPMA) copolymers, polyacrylic acids, polyacrylamides, polyoxazolines, divinyl ether-maleic anhydride, polyphosphazenes, including derivatives and substitutions, and combinations thereof.

Preferably, the adhesion enhancing agent is a maltodextrin and/or a cellulose and/or starch and/or a gum.

In one aspect, the adhesion enhancing agent is based on starch or cellulose.

A "pH adjusting agent" is typically added to bring the pH of the composition to the desired value. Desirable pH values are between about 6 to about 8. The compositions of the described invention therefore may be formulated to have a pH value that ranges between about 6 and about 8, or about 6.5 and about 7.5. Suitable pH adjusting agents include, but are not limited to, one or more adipic acids, glycines, citric acids, calcium hydroxides, magnesium aluminometasilicates, disodium phosphate, sodium phosphate, potassium phosphate, potassium chloride, sodium citrate, calcium lactate, sodium succinate, sodium glutamate, sodium bicarbonate, and potassium bicarbonate, and combinations thereof.

As used herein, "stabilizer" is an agent that helps stabilize the active agent in the composition. The stabilizer includes but is not limited to reducing agents. Stabilizers that may be used include sodium thiosulfate, sodium metabisulfite, sodium bisulfite, sodium sulfite, sulphur dioxide, ammonium bisulfite, and ammonium thiosulfate. Sodium thiosulfate is preferred as it possess a high neutralization ability and is considered safe and not corrosive.

The term "stabilizer" also encompasses Chelating agents. Chelating agents are optionally added to the compositions of the described invention to enhance the preservative or preservative system. Preferred chelating agents are mild agents, such as, for example, ethylenediaminetetraacetic acid (EDTA), EDTA derivatives, or any combination thereof.

Suitable stabilizers or preservatives for use in the compositions of the present composition include, without limitation, one or more alkanols, disodium EDTA (ethylenediamine tetraacetate), EDTA salts, EDTA fatty acid conjugates, isothiazolinone, parabens such as methylparaben and propylparaben, propylene glycols, sorbates, urea derivatives such as diazolindinyl urea, or any combinations thereof.

In one aspect of the present invention the gel composition comprises water, an adhesion enhancing agent and a stabilizer.

In one aspect of the present invention the gel composition comprises water, an adhesion enhancing agent and a stabilizer and a pH adjusting agent.

In one aspect of the present invention the gel composition further comprises a flavoring agent and/or a colorant.

The term "colorant" also may be used in the compositions of the described invention to provide visual cues to the piglets and/or visual verification to animal caretakers that the composition is present, uniformly applied and appropriately adherent. Colorants are well known to the person skilled in the art and include pigments or dyes or a combination thereof. Suitable colorants include, but are not limited to FD&C colorants such as FD&C Blue No. 1, FD&C Blue No. 2, FD&C Green No. 3, Orange B, Citrus FD&C Red No. 2, FD&C Red No. 2, FD&C Red No. 3. FD&C Red No. 40, FD&C Yellow No. 5 and FD&C Yellow No. 6.

The term "flavoring agent" as used herein refers to one or more compounds or mixtures that improve the palatability and/or taste in animals or swine. Flavoring agents are well known to the person skilled in the art. Flavoring agents include but are not limited to nutritive and non-nutritive sweeteners, flavor additives, by-products and alternative ingredients. By way of example suitable flavorants include but are not limited to sucrose, glucose, sodium saccharin, sodium cyclamate, xylitol, perillartien, sucralose, D-tryptophan, aspartame, dihydrochalcones and the like, artificial fruit flavoring (e.g., strawberry flavoring), plasma protein (e.g., spray-dried plasma protein), cheese and cheese-like flavorings, dried milk, chocolate and chocolate by-products.

In one aspect of the present invention the gel composition comprises water, maltodextrins, cellulose, a gum and a stabilizer, preferably the stabilizer is propylene glycol.

In one aspect of the present invention the gel composition comprises water, maltodextrins, hemicellulose extract, gum acacia and propylene glycol.

In one aspect of the present invention the gel composition comprises water, maltodextrins, hemicellulose extract, water stabilizing compounds, gum acacia, propylene glycol and artificial coloring.

In one aspect of the present invention the immunogenic gel composition further comprises a veterinary-acceptable carrier.

In one aspect of the present invention the veterinary-acceptable carrier is a diluent.

"Diluent" can include water, saline, dextrose, ethanol, glycerol, and the like. Isotonic agents can include sodium chloride, dextrose, mannitol, sorbitol, and lactose, among others. Stabilizers include albumin and alkali salts of ethylenediaminetetraacetic acid, among others.

In one aspect of the present invention the veterinary-acceptable carrier is a physiologic buffer.

In one aspect of the present invention the pharmaceutically acceptable carrier is phosphate buffered saline.

Preferably, the immunogenic composition further comprises sucrose gelatin stabilizer.

Preferably, the immunogenic composition can further include one or more other immunomodulatory agents such as, e.g. interleukins, interferons, or other cytokines. The amounts and concentrations of adjuvants and additives useful in the context of the present invention can readily be determined by the skilled artisan.

In one aspect of the present invention said veterinary-acceptable carrier is selected from the group consisting of solvents, dispersion media, coatings, stabilizing agents, diluents, preservatives, antibacterial and antifungal agents, isotonic agents, adsorption delaying agents, adjuvants, immune stimulants, and combinations thereof.

In some aspects, the immunogenic composition of the present invention contains an adjuvant. "Adjuvants" as used herein, can include aluminum hydroxide and aluminum phosphate, saponins e.g., Quil A, QS-21 (Cambridge Biotech Inc., Cambridge MA), GPI-0100 (Galenica Pharmaceuticals, Inc., Birmingham, AL), water-in-oil emulsion, oil-in-water emulsion, water-in-oil-in-water emulsion. The emulsion can be based in particular on light liquid paraffin oil (European Pharmacopea type); isoprenoid oil such as squalane or squalene; oil resulting from the oligomerization of alkenes, in particular of isobutene or decene; esters of acids or of alcohols containing a linear alkyl group, more particularly plant oils, ethyl oleate, propylene glycol di-(caprylate/caprate), glyceryl tri-(caprylate/caprate) or propylene glycol dioleate; esters of branched fatty acids or alcohols, in particular isostearic acid esters. The oil is used in combination with emulsifiers to form the emulsion. The emulsifiers are preferably nonionic surfactants, in particular esters of sorbitan, of mannide (e.g. anhydromannitol oleate), of glycol, of polyglycerol, of propylene glycol and of oleic, isostearic, ricinoleic or hydroxystearic acid, which are optionally ethoxylated, and polyoxypropylene-polyoxyethylene copolymer blocks, in particular the Pluronic products, especially L121. See Hunter et al., The Theory and Practical Application of Adjuvants (Ed.Stewart-Tull, D. E. S.), JohnWiley and Sons, NY, pp 51-94 (1995) and Todd et al., Vaccine 15:564-570 (1997). Exemplary adjuvants are the SPT emulsion described on page 147 of "Vaccine Design, The Subunit and Adjuvant Approach" edited by M. Powell and M. Newman, Plenum Press, 1995, and the emulsion MF59 described on page 183 of this same book.

A further instance of an adjuvant is a compound chosen from the polymers of acrylic or methacrylic acid and the copolymers of maleic anhydride and alkenyl derivative. Advantageous adjuvant compounds are the polymers of acrylic or methacrylic acid which are cross-linked, especially with polyalkenyl ethers of sugars or polyalcohols. These compounds are known by the term carbomer (Phameuropa Vol. 8, No. 2, June 1996). Persons skilled in the art can also refer to U.S. Pat. No. 2,909,462 which describes such acrylic polymers cross-linked with a polyhydroxylated compound having at least 3 hydroxyl groups, preferably not more than 8, the hydrogen atoms of at least three hydroxyls being replaced by unsaturated aliphatic radicals having at least 2 carbon atoms. The preferred radicals are those containing from 2 to 4 carbon atoms, e.g. vinyls, allyls and other ethylenically unsaturated groups. The unsaturated radicals may themselves contain other substituents, such as methyl. The products sold under the name Carbopol; (BF Goodrich, Ohio, USA) are particularly appropriate. They are cross-linked with an allyl sucrose or with allyl pentaerythritol. Among then, there may be mentioned Carbopol 974P, 934P and 971P. Most preferred is the use of Carbopol 971P. Among the copolymers of maleic anhydride and alkenyl derivative, are the copolymers EMA (Monsanto), which are copolymers of maleic anhydride and ethylene. The dissolution of these polymers in water leads to an acid solution that will be neutralized, preferably to physiological pH, in order to give the adjuvant solution into which the immunogenic, immunological or vaccine composition itself will be incorporated.

Further suitable adjuvants include, but are not limited to, the RIBI adjuvant system (Ribi Inc.), Block co-polymer (CytRx, Atlanta GA), SAF-M (Chiron, Emeryville CA), monophosphoryl lipid A, Avridine lipid-amine adjuvant, heat-labile enterotoxin from E. coli (recombinant or otherwise), cholera toxin, IMS 1314 or muramyl dipeptide, or naturally occurring or recombinant cytokines or analogs thereof or stimulants of endogenous cytokine release, among many others.

It is expected that an adjuvant can be added in an amount of about 100 μg to about 10 mg per dose, preferably in an amount of about 100 μg to about 10 mg per dose, more preferably in an amount of about 500 μg to about 5 mg per dose, even more preferably in an amount of about 750 μg to about 2.5 mg per dose, and most preferably in an amount of about 1 mg per dose. Alternatively, the adjuvant may be at a concentration of about 0.01 to 50%, preferably at a concentration of about 2% to 30%, more preferably at a concentration of about 5% to 25%, still more preferably at a concentration of about 7% to 22%, and most preferably at a concentration of 10% to 20% by volume of the final product.

In one aspect of the present invention said veterinary-acceptable carrier is an adjuvant selected from the group consisting of aluminum hydroxide, aluminum phosphate, saponins, water-in-oil emulsion, oil-in-water emulsion, water-in-oil-in-water emulsion, polymers of acrylic or methacrylic acid, copolymers of maleic anhydride and alkenyl derivative, the RIBI adjuvant system, Block co-polymer, SAF-M, monophosphoryl lipid A, Avridine lipid-amine, heat-labile enterotoxin from *E. coli* (recombinant or otherwise), cholera toxin, IMS 1314, muramyl dipeptide, and combinations thereof.

In one aspect of the present invention said veterinary-acceptable carrier is a water-in-oil-in-water emulsion or a carbomer.

In one aspect of the present invention the immunogenic gel composition is vaccine gel composition.

Method of Treatment Claims

Further, the present invention provides a method of immunizing an animal comprising administering to said animal a therapeutically effective amount of an immunogenic gel composition comprising an antigen of an animal pathogen and a gel composition for oral administration.

Thus, the present invention provides an immunogenic gel composition comprising an antigen of an animal pathogen and a gel composition for oral administration for use in a method of immunizing an animal, the method comprises administering to said animal a therapeutically effective amount of said immunogenic gel composition.

Further, the present invention provides a method of treating or preventing clinical signs caused by an animal pathogen in an animal, the method comprising administering to said animal a therapeutically effective amount of an immunogenic gel composition comprising an antigen of an animal pathogen and a gel composition for oral administration.

Thus, the present invention provides an immunogenic gel composition comprising an antigen of an animal pathogen and a gel composition for oral administration for use in a method of treating or preventing clinical signs caused by an animal pathogen in an animal, the method comprises administering to said animal a therapeutically effective amount of said immunogenic gel composition.

Further, the present invention provides a method of immunizing an animal, the method comprises administering to said animal a therapeutically effective amount of an immunogenic gel composition as described herein.

Thus, the present invention provides an immunogenic gel composition as described herein for use in a method of immunizing an animal, the method comprises administering to said animal a therapeutically effective amount of said immunogenic gel composition.

Further, the present invention provides a method of treating or preventing clinical signs caused by *Lawsonia intracellularis* and/or *Salmonella* spp. in an animal, the method comprising administering to said animal a therapeutically effective amount of an immunogenic gel composition as described herein.

Thus, the present invention provides an immunogenic gel composition as described herein for use in a method of treating or preventing clinical signs caused by *Lawsonia intracellularis* and/or *Salmonella* spp. in an animal, the method comprises administering to said animal a therapeutically effective amount of said immunogenic gel composition.

Further, the present invention provides a method for reducing lesions in the intestine in an animal, in comparison to an animal of a non-immunized control group of the same species, the method comprises administering to said animal an effective amount of the immunogenic gel composition as described herein.

Thus, the present invention provides an immunogenic gel composition as described herein for use in a method for reducing lesions in the intestine in an animal, in comparison to an animal of a non-immunized control group of the same species, the method comprises administering to said animal a therapeutically effective amount of said immunogenic gel composition.

Further, the present invention provides a method of increasing the average daily weight gain of an animal, in comparison to an animal of a non-immunized control group of the same species, the method comprises administering to said animal an effective amount of the immunogenic gel composition Thus, the present invention provides an immunogenic gel composition as described herein for use in a method of increasing the average daily weight gain of an animal, the method comprises administering to said animal a therapeutically effective amount of said immunogenic gel composition.

Advantageously, the experimental data provided herein disclose that the animals consumed the vaccine gel compositions. The uptake of the live *Salmonella* and *Lawsonia intracellularis* antigens of the gel vaccine composition was even superior compared to the conventional oral drench method of oral administration. Further, the vaccine gel compositions were as efficacious as the conventional application methods.

However, advantageously, animals were vaccinated earlier in time, within the medication free window (during the suckling period), with none or reduced individual pig handling, reduced labor and reduced stress for the animals.

The term "preventing" generally involves the administration of an effective amount of the immunogenic gel composition of the present invention to an animal or herd of animals in need of or that could benefit from such a treatment/prophylaxis. The term "treatment" refers to the administration of the effective amount of the immunogenic composition once the animal or at least some animals of the herd is/are already infected with such animal pathogen and wherein such animals already show some clinical signs caused by or associated with such animal pathogen infection. The term "prophylaxis" refers to the administration of an animal prior to any infection of such animal with an animal pathogen or at least where such animal or none of the animals in a group of animals do not show any clinical signs caused by or associated with the infection by such animal pathogen. The terms "preventing" and "treatment and/or prophylaxis" are used interchangeable in this application.

As used herein, the term "effective amount" means, in the context of a composition, an amount of an immunogenic gel composition capable of inducing an immune response that reduces the incidence of or lessens the severity of infection or incident of disease in an animal. Such effective amount is able to lessen the incidence of the particular animal pathogen infection in a herd or to reduce the severity of clinical signs of the particular animal pathogen infection. Particularly, an effective amount refers to $TCID_{50}$ per dose. Alternatively, in the context of a therapy, the term "effective amount" refers to the amount of a therapy which is sufficient to reduce or ameliorate the severity or duration of a disease or disorder, or one or more symptoms thereof, prevent the advancement of a disease or disorder, cause the regression of a disease or disorder, prevent the recurrence, development, onset, or progression of one or more symptoms associated with a disease or disorder, or enhance or improve the prophylaxis or treatment of another therapy or therapeutic agent.

The term "clinical signs" of *Lawsonia intracellularis* infection as used herein includes, but is not limited to a reduced average daily weight gain (ADWG), increased variability in weight gain, increased feed conversion ratio, gross lesions in ileum and/or jejunum and/or cecum and/or colon, diarrhea, death, detectable bacterial load, shedding of *Lawsonia intracellularis* or combinations thereof.

The term "clinical signs" of *Salmonella* spp. infection as used herein includes, but is not limited to a reduced average daily weight gain (ADWG), increased variability in weight gain, increased feed conversion ratio, gross lesions in ileum and/or Jeejnum and/or cecum and/or colon, diarrhea, worsening of body condition, depressive or lethargic behavior, detectable bacterial load, shedding of *Salmonella* or combinations thereof.

Preferably, clinical signs are reduced in incidence or severity by at least 10%, more preferably by at least 20%, still more preferably by at least 30%, even more preferably by at least 40%, still more preferably by at least 50%, even more preferably by at least 60%, still more preferably by at least 70%, even more preferably by at least 80%, still more preferably by at least 90%, still more preferably by at least 95% and most preferably by 100% in comparison to animals that are either not treated or treated with an immunogenic composition that was available prior to the present invention but subsequently infected by the particular animal pathogen. However, "reduction of the incidence and/or severity of clinical signs" or "reduction of clinical symptoms" means, but is not limited to, reducing the number of infected animals in a group, reducing or eliminating the number of animals exhibiting clinical signs of infection, or reducing the severity of any clinical signs that are present in one or more animals, in comparison to wild-type infection.

In one aspect of the present invention the animal pathogen is a swine, horse or cattle pathogen.

In one aspect of the present invention the animal pathogen is a bacterial swine or cattle pathogen.

In one aspect of the present invention the animal pathogen is an enteric disease-causing bacteria or a mucosal disease-causing bacteria.

Enteric disease-causing bacteria or mucosal disease-causing bacteria are well known in the art and exemplarily encompass *Salmonella* spp., *E. coli*, *Lawsonia intracellularis* and *Brachyspira* spp.

In one aspect of the present invention the animal pathogen is *Salmonella* spp., *E. coli*, *Lawsonia intracellularis*, *Brachyspira* spp. or *Clostridium* spp.

In one aspect of the present invention said antigen of an animal pathogen is a mucosal or enteric active antigen or a mucosal or enteric active live immunogenic composition or a mucosal or enteric active live vaccine.

The term "mucosal or enteric active antigen" means that said antigen will cause an immune response in the mucosa and/or epithelial cells and/or enterocytes or will activate the mucosal or gastrointestinal immune system.

In one aspect of the present invention said antigen of an animal pathogen is a mucosal or enteric active antigen from swine or cattle.

The term "animal" refers preferably to mammals such as mice, rats, guinea pigs, rabbits, hamsters, swine, sheep, dogs, cats, horses, monkeys, or cattle. More preferably, the animal is a swine.

It has to be understood that the term "pig" or "swine" comprises piglets, sows, gilts, boars and the alike.

In one aspect of the present invention the animal is a swine, horse or cattle.

In one aspect of the present invention the animal is a pig, piglet, sow or swine.

In one aspect of the present invention the animal is a neonatal pig or a piglet prior to weaning.

In one aspect of the present invention the immunogenic gel composition is administered to the animal one day of age onwards, three days of age onwards or one week of age onwards or two weeks of age onwards or three weeks of age onwards.

In one aspect of the present invention the immunogenic gel composition is administered to the animal one day of age onwards, three days of age onwards, one week of age onwards or two weeks of age onwards.

In one aspect of the present invention the immunogenic gel composition is administered to the animal between one week of age and three weeks of age.

In one aspect of the present invention the immunogenic gel composition is administered to the animal between 6 days of age and 20 days of age.

In one aspect of the present invention the immunogenic gel composition is administered to the animal between 8 days of age and 18 days of age or between 10 days of age and 16 days of age.

In one aspect of the present invention the immunogenic gel composition further comprises a veterinary-acceptable carrier.

In one aspect of the present invention the immunogenic gel composition is administered once or in two doses.

In one aspect of the present invention the immunogenic gel composition is administered in multiple doses.

It has furthermore been shown that administration of one dose of the immunogenic gel composition of the present invention is effective.

In one aspect of the present invention the immunogenic gel composition is administered by oral and/or a mucosal route.

The term "administering" or "administration" as used herein means that the immunogenic gel composition is administered indirectly to the animals. The immunogenic gel composition is directly applied somewhere within the barn or housing environment to allow said animal to consume said immunogenic gel composition. The immunogenic gel composition can also be applied to a mother animal to allow said animal to consume said immunogenic gel composition. By this method, advantageously, animals were vaccinated earlier in time, within the medication free window (during the suckling period), with none or reduced individual pig handling, reduced labor and reduced stress for the animals.

Preferably, an applicator gun or a drench gun is used. Preferably, a 60 ml or a 120 ml or bigger applicator gun or a drench gun is used. Using such applicator gun or a drench gun enables to easily apply defined amounts of the immunogenic gel composition onto the animal (such as the underline) or into the barn (such as onto the mat).

In one aspect of the present invention the method comprises applying the immunogenic gel composition within the barn or housing environment to allow said animal to consume said immunogenic gel composition.

It has to be understood that the immunogenic gel composition can be placed at any place in the environment of the animals or within the barn that allows said animal to consume said immunogenic gel composition.

In one aspect of the present invention the method comprises applying said immunogenic gel composition to the underline of a mother animal or an udder of a mother animal, to a mat within the barn or in a cup or vessel within the barn.

Preferably, the immunogenic gel composition is applied onto the mat. Applying the immunogenic gel composition onto the mat is advantageously because the handling is easy and fast with no individual pig handling, reduced labor and reduced stress for the animals.

In one aspect of the present invention the method comprises applying said immunogenic gel composition to a mat within the barn.

In one aspect of the present invention the method comprises topically applying the immunogenic gel composition to a mother animal and allowing a neonatal animal or an animal prior to weaning to consume said immunogenic gel composition.

In one aspect of the present invention the method comprises topically applying said immunogenic gel composition to the underline of a mother animal or wherein the method comprises topically applying said immunogenic gel composition to at least one teat of a mother animal.

In one aspect of the present invention the mother animal is a sow.

In one aspect of the present invention the neonatal animal is a neonatal piglet.

In one aspect of the present invention the animal prior to weaning is a piglet prior to weaning.

In one aspect of the present invention said method results in an improvement in an efficacy parameter selected from the group consisting of: a reduction in weight loss, a lower bacterial load, a reduction in intestinal lesions, a reduction in colon lesions, a reduction in ileum and/or jejunum lesions, a reduced shedding, a reduction in diarrhea, or combinations thereof, in comparison to an animal of a non-immunized control group of the same species.

Preferably, said lesions mean macroscopic and/or microscopic lesions.

The term "reducing" or "reduction" means that the incidence and/or severity of the particular clinical signs is reduced by at least 10%, preferably by at least 20%, more preferably by at least 30%, even more preferably by at least 40%, even more preferably by at least 50%, even more preferably by at least 60%, even more preferably by at least 70%, even more preferably by at least 80%, even more preferably by at least 90%, even more preferably by at least 95% and most preferably by 100% as compared to an animal of a non-immunized control group of the same species.

In one aspect of the present invention the immunogenic gel composition is a vaccine gel composition.

In one aspect of the present invention the immunogenic gel composition further comprises a veterinary-acceptable carrier.

In one aspect of the present invention the gel composition is the gel composition as described herein.

Further, the present invention provides a mat comprising the gel composition as described herein.

DISCLOSURE

The Disclosure Further Comprises:

An immunogenic gel composition comprising a *Lawsonia intracellularis* antigen and/or a *Salmonella* spp. antigen and a gel composition suitable for oral administration.

In any of the aforementioned disclosure of the immunogenic gel composition said *Lawsonia intracellularis* antigen and/or the *Salmonella* spp. antigen are whole cell bacteria.

In any of the aforementioned disclosure of the immunogenic gel composition said *Lawsonia intracellularis* antigen is modified live *Lawsonia intracellularis*.

In any of the aforementioned disclosure of the immunogenic gel composition said *Lawsonia intracellularis* antigen is an avirulent isolate of *Lawsonia intracellularis* or an attenuated *Lawsonia intracellularis*.

In any of the aforementioned disclosure of the immunogenic gel composition said immunogenic gel composition comprises about 3.0 to about 9.0 $TCID_{50}$ of the modified live *Lawsonia intracellularis* per dose.

In any of the aforementioned disclosure of the immunogenic gel composition said *Salmonella* spp. antigen is modified live *Salmonella* spp.

In any of the aforementioned disclosure of the immunogenic gel composition said *Salmonella* spp. is *Salmonella Choleraesuis* and/or *Salmonella Typhimurium*.

In any of the aforementioned disclosure of the immunogenic gel composition said *Salmonella* spp. is *Salmonella enterica* subsp. *enterica* serovar *Choleraesuis* and/or *Salmonella enterica* subsp. *enterica* serovar *Typhimurium*.

In any of the aforementioned disclosure of the immunogenic gel composition said immunogenic gel composition comprises about $1 \times 10^5$ to about $1 \times 10^{10}$ CFU of the *Salmonella* spp. per dose.

In any of the aforementioned disclosure of the immunogenic gel composition said gel composition is viscous or has a viscosity of at least 50 mPa·s or at least 50 cP.

In any of the aforementioned disclosure of the immunogenic gel composition said gel composition comprises water and/or an adhesion enhancing agent and/or a pH adjusting agent and/or a stabilizer.

In any of the aforementioned disclosure of the immunogenic gel composition said gel composition comprises water, an adhesion enhancing agent and a stabilizer.

In any of the aforementioned disclosure of the immunogenic gel composition said gel composition further comprises a flavoring agent and/or a colorant.

In any of the aforementioned disclosure of the immunogenic gel composition said gel composition comprises water, maltodextrins, cellulose, a gum and a stabilizer, preferably the stabilizer is propylene glycol.

In any of the aforementioned disclosure of the immunogenic gel composition said gel composition comprises water, maltodextrins, hemicellulose extract, gum acacia and propylene glycol.

In any of the aforementioned disclosure of the immunogenic gel composition said gel composition comprises water, maltodextrins, hemicellulose extract, water stabilizing compounds, gum acacia, propylene glycol and artificial coloring.

In any of the aforementioned disclosure of the immunogenic gel composition said immunogenic gel composition further comprises a veterinary-acceptable carrier.

In any of the aforementioned disclosure of the immunogenic gel composition said immunogenic gel composition is vaccine gel composition.

In any of the aforementioned disclosure of the immunogenic gel composition said

The Disclosure Further Comprises:

A method of immunizing an animal comprising administering to said animal a therapeutically effective amount of an immunogenic gel composition comprising an antigen of an animal pathogen and a gel composition for oral administration The Disclosure Further Comprises:

A method of treating or preventing clinical signs caused by an animal pathogen in an animal, the method comprising administering to said animal a therapeutically effective amount of an immunogenic gel composition comprising an antigen of an animal pathogen and a gel composition for oral administration.

The Disclosure Further Comprises:

A method of immunizing an animal comprising administering to said animal a therapeutically effective amount of an immunogenic gel composition as described herein.

The Disclosure Further Comprises:

A method of treating or preventing clinical signs caused by *Lawsonia intracellularis* and/or *Salmonella* spp. in an animal, the method comprising administering to said animal a therapeutically effective amount of an immunogenic gel composition as described herein.

The Disclosure Further Comprises:

A method for reducing lesions in the intestine in an animal, in comparison to an animal of a non-immunized control group of the same species, comprising administering to said animal an effective amount of the immunogenic gel composition as described herein.

The Disclosure Further Comprises:

A method of increasing the average daily weight gain of an animal, in comparison to an animal of a non-immunized control group of the same species, comprising administering to said animal an effective amount of the immunogenic gel composition as described herein.

In any of the aforementioned disclosure of the method said animal pathogen is a swine, horse or cattle pathogen.

In any of the aforementioned disclosure of the method said animal pathogen is a bacterial swine or cattle pathogen.

In any of the aforementioned disclosure of the method said animal pathogen is an enteric disease-causing bacteria or a mucosal disease-causing bacteria.

In any of the aforementioned disclosure of the method said antigen of an animal pathogen is a mucosal or enteric active antigen or a mucosal or enteric active live immunogenic composition or a mucosal or enteric active live vaccine.

In any of the aforementioned disclosure of the method said animal is a swine, horse or cattle.

In any of the aforementioned disclosure of the method said animal is a pig, piglet, sow or swine.

In any of the aforementioned disclosure of the method said animal is a neonatal pig or a piglet prior to weaning.

In any of the aforementioned disclosure of the method said immunogenic gel composition is administered to the animal one day of age onwards, three days of age onwards or one week of age onwards or two weeks of age onwards or three weeks of age onwards or, wherein, the immunogenic gel composition is administered to the animal between 6 days of age and 20 days of age.

In any of the aforementioned disclosure of the method said immunogenic gel composition further comprises a veterinary-acceptable carrier.

In any of the aforementioned disclosure of the method said immunogenic gel composition is administered once or in two doses In any of the aforementioned disclosure of the method said immunogenic gel composition is administered by oral and/or a mucosal route.

In any of the aforementioned disclosure of the method said method comprises applying the immunogenic gel composition within the barn or housing environment to allow said animal to consume said immunogenic gel composition.

In any of the aforementioned disclosure of the method said method comprises applying said immunogenic gel composition to the underline of a mother animal or an udder of a mother animal, to a mat within the barn or in a cup or vessel within the barn.

In any of the aforementioned disclosure of the method said method comprises applying said immunogenic gel composition to a mat within the barn.

In any of the aforementioned disclosure of the method said method comprises topically applying the immunogenic gel composition to a mother animal and allowing a postnatal animal or an animal prior to weaning to consume said immunogenic gel composition.

In any of the aforementioned disclosure of the method said method comprises topically applying said immunogenic gel composition to the underline of a mother animal or wherein the method comprises topically applying said immunogenic gel composition to at least one teat of a mother animal.

In any of the aforementioned disclosure of the method said mother animal is a sow and/or the postnatal animal is a postnatal piglet and/or the animal prior to weaning is a piglet prior to weaning.

In any of the aforementioned disclosure of the method said method results in an improvement in an efficacy parameter selected from the group consisting of: a reduction in weight loss, a lower bacterial load, a reduction in intestinal lesions, a reduction in colon lesions, in cecum lesions a reduction in ileum and/or jejunum lesions, a reduced shedding, a reduction in diarrhea, or combinations thereof, in comparison to a subject of a non-immunized control group of the same species.

In any of the aforementioned disclosure of the method said immunogenic gel composition is a vaccine gel composition.

In any of the aforementioned disclosure of the method said immunogenic gel composition further comprises a veterinary-acceptable carrier.

In any of the aforementioned disclosure of the method said gel composition is the gel composition as described herein.

The Disclosure Further Comprises:

A mat comprising the gel composition as described herein.

EXAMPLES

The following examples are only intended to illustrate the present invention. They shall not limit the scope of the claims in any way.

Example 1

Evaluation of Gel Vaccine Uptake by Evaluation of Vaccine Shedding Following Different Forms of Administration of MLV *Lawsonia Intracellularis* or *Salmonella*

The objective of this study is to evaluate whether an oral vaccine given in a gel formulation, applied to different locations of the housing environment, is efficiently taken up by the animals and how it compares to the conventional method of oral administration by oral drench.

Enterisol® Ileitis (commercially available *Lawsonia intracellularis* live vaccine) is mixed with a gel composition (Underline® gel, is commercially available and comprises water, maltodextrins, propylene glycol, hemicellulose extract, however, other gel compositions are suitable as well).

Treatment Groups (40 pigs per group):
Group 1: Enterisol® Ileitis applied in gel on udder of sow.
Group 2: Enterisol® Ileitis applied in gel in cup.
Group 3: Enterisol® Ileitis applied in gel to mat.
Group 4: Enterisol® Ileitis applied by oral drench.
Group 5: Non-vaccinated, negative control.

Because Enterisol® Ileitis is an oral MLV (modified live vaccine) *Lawsonia* vaccine, *Lawsonia* bacteria are shed via feces. The efficacy of the vaccine uptake is evaluated by measuring the shedding of *Lawsonia intracellularis* in feces by vaccinated pigs by quantitative PCR which is a standard procedure in the art.

TABLE 1

| Treatment Group | Shedding in % |
|---|---|
| Group 1: Enterisol ® Ileitis applied in gel on udder | 46.15 |
| Group 2: Enterisol ® Ileitis applied in gel in cup | 44.40 |
| Group 3: Enterisol ® Ileitis applied in gel to mat | 33.3 |
| Group 4: Enterisol ® Ileitis applied by oral drench | 15.79 |
| Group 5: Non-vaccinated, negative control | 0 |

In a further experiment, the gel administration of another oral MLV (modified live vaccine) is tested. Enterisol® *Salmonella* T/C (T/C) (commercially available *Salmonella* live vaccine) is mixed with a gel composition (Underline® gel, commercially available from Animal Science Products, Inc. Nacogdoches, TX). The vaccine is given via gel or via oral drench and the efficacy of the vaccine uptake is evaluated by measuring the shedding of *Salmonella* bacteria in feces.

Treatment Groups (24 pigs per group):
Group 1: Non-vaccinated, negative control.
Group 2: Enterisol® *Salmonella* T/C is applied in gel to a mat.
Group 3: Enterisol® *Salmonella* T/C is applied by oral drench.

TABLE 2

| Treatment Group | Shedding % |
|---|---|
| Group 1: Non-vaccinated, negative control | 0% |
| Group 2: Enterisol *Salmonella* T/C applied in gel to mat | 33% |
| Group 3: Enterisol *Salmonella* T/C Oral Drench Administration | 4% |

Conclusion

Oral vaccines administered in a gel formulation are efficiently taken up by the animals.

The uptake of the MLV *Lawsonia intracellularis* or MLV *Salmonella* administered in the gel composition was surprisingly even higher compared to the standard oral drench administration.

Example 2

Evaluation of MLV *Lawsonia Intracellularis* Efficacy Administered Orally by Gel with a *Lawsonia Intracellularis* Challenge The objective of this study is to evaluate the effectiveness of a gel composition as means for oral administration of Enterisol vaccines. To validate this approach, vaccine efficacy when administered orally through gel is assessed by experimental challenge. Enterisol® Ileitis (commercially available *Lawsonia intracellularis* live vaccine) is mixed with a gel composition (Underline® gel, commercially available) and applied to the farrowing crate mat at pigs being 14-16 days of age. Pigs are challenged with *Lawsonia intracellularis* 49 days after vaccination. Efficacy is measured using individual pig differences in gross lesions, microscopic lesions, IHC scores as primary variables.

Sows are *Lawsonia intracellularis* PCR negative. The non-vaccinated treatment group litters are housed in a separate farrowing room than vaccinated treatment groups to control and prevent exposure to the vaccine. Each treatment comprises of 6 pigs selected from 4 litters. The Study evaluates Underline gel for the administration of Enterisol Ileitis (EI). For this objective, three different treatment groups are used 1) Non-vaccinated, *Lawsonia intracellularis* challenged Control, 2) EI gel administration, 3) EI gel administration, 4) EI Oral drench administration.

Treatment Groups

TABLE 3

| Treatment | Treatment Name | Treatment Description | Treatment Dose | Route of Administration |
|---|---|---|---|---|
| 1 | Non-vaccinated, *L. intracellularis* challenged control | Non-vaccinated, challenged controls | NA | NA |
| 2 | Enterisol ® Ileitis Underline ® Gel administration | Pigs vaccinated with Enterisol ® Ileitis via Underline ® Gel applied on the mat at 14-16 days of age, challenged 49 days later | 120 mL/farrowing crate, approximately 10 mL/piglet assuming 12 piglets/litter; full dose | Oral |
| 3 | Enterisol ® Ileitis Underline ® Gel administration | Pigs vaccinated with Enterisol ® Ileitis via Underline ® Gel applied on the mat at 14-16 days of age, challenged 49 days later | 120 mL/farrowing crate, approximately 10 mL/piglet assuming 12 piglets/litter; full dose | Oral |

TABLE 3-continued

| Treatment | Treatment Name | Treatment Description | Treatment Dose | Route of Administration |
|---|---|---|---|---|
| 4 | Enterisol ® Ileitis oral drench administration | Pigs vaccinated with Enterisol ® Ileitis via oral drench at 14-16 days of age, challenged 49 days later | 1 mL; full dose | Oral |

The vaccine is administered to piglets at 14-16 days of age. Piglets are weaned at 21-24 days of age. Challenge with *Lawsonia* gut homogenate is done 7 weeks post-vaccination with a wild-type isolate (Challenge dose of $2.76 \times 10^{10}$ *L. intracellularis* organisms/pig). Vaccine efficacy is assessed by macroscopic and microscopic lesions. The jejunum, ileum, cecum, and colon are examined and scored for gross lesions characteristic of enteric disease and *Lawsonia* infection. Macroscopic lesions are evaluated following the rubric: 0=no gross lesion; 1=mild edema and hyperemia of mucosa or serosa; 2=edema, hyperemia, reticulated serosa and mucosa (thickening); 3=edema, hyperemia, reticulated serosa and mucosa and gross thickening of the mucosa; 4=severe thickening mucosal hemorrhaging or necrosis. The length of the macroscopic lesions are also recorded. The distal ileum is formalin fixed for microscopic histopathology and immunohistochemistry (IHC) staining for *Lawsonia intracellularis* is evaluated on a five point scale as follows: 0=absence of *Lawsonia* antigen; 1=0-25% of crypts with antigen; 2=25-50% of crypts with antigen; 3=50-75% of crypts with antigen; 4=75-100% of crypts with antigen. Hematoxylin and eosin stain is evaluated with the following rubric: 0=no lesions; 1=focal lesions; 2=multifocal lesions, 3=diffuse lesions.

TABLE 4

Results Gross Lesions Average Score Per Treatment Group

| Average Score | Treatment 1: Control | Treatment 2: EI Vx Gel | Treatment 3: EI Vx Gel | Treatment 4: EI Vx Oral Drench |
|---|---|---|---|---|
| Ileum | 0.90 ± 0.29 | 0.79 ± 0.27 | 0.50 ± 0.20 | 0.57 ± 0.23 |
| Jejunum | 0.62 ± 0.28 | 0.67 ± 0.26 | 0.17 ± 0.13 | 0.48 ± 0.20 |
| Caecum | 0.38 ± 0.19 | 0.33 ± 0.17 | 0.25 ± 0.17 | 0 ± 0 |
| Colon | 0.14 ± 0.10 | 0.08 ± 0.08 | 0 ± 0 | 0 ± 0 |

Vx = vaccine

TABLE 5

Results Gross Lesions Average Length Per Treatment Group

| Average Length | Treatment 1: Control | Treatment 2: EI Vx Gel | Treatment 3: EI Vx Gel | Treatment 4: EI Vx Oral Drench |
|---|---|---|---|---|
| Ileum length, cm | 6.33 ± 1.98 | 5.83 ± 1.82 | 3.17 ± 1.30 | 4.35 ± 1.76 |
| Jejunum length, cm | 26.90 ± 11.59 | 11.67 ± 7.02 | 10.13 ± 9.70 | 12.26 ± 8.26 |
| Caecum length, cm | 2.38 ± 1.18 | 1.67 ± 0.78 | 0.83 ± 0.58 | 0 ± 0 |
| Colon length, cm | 2.62 ± 2.17 | 0.83 ± 0.83 | 0 ± 0 | 0 ± 0 |

TABLE 6

Results IHC and H&E Scores

| Average Score | Treatment 1: Control | Treatment 2: EI Vx Gel | Treatment 3: EI Vx Gel | Treatment 4: EI Vx Oral Drench |
|---|---|---|---|---|
| IHC | 3.52 ± 0.16 | 2.63 ± 0.25 | 2.50 ± 0.26 | 1.74 ± 0.33 |
| H&E | 2.76 ± 0.14 | 2.17 ± 0.22 | 2.25 ± 0.21 | 1.30 ± 0.26 |

Conclusion

Modified live *Lawsonia intracellularis* can be administered by gel compositions for the immunization of pigs. Enterisol® Ileitis administered both by oral drench or by gel reduces gross lesions and reduces IHC scores compared to the non-vaccinated challenge control group.

Example 3

Evaluation of MLV *Salmonella* T/C Efficacy Administered Orally by Gel with a *Salmonella Typhimurium* Challenge The objective of this study is to evaluate the effect of Enterisol® *Salmonella* T/C (T/C) administered by Underline® gel. The composition is applied to the farrowing crate mat at pigs 14 days of age. 28 days after vaccination, pigs are challenged with *Salmonella Typhimurium*. Efficacy is measured using individual pig differences in gross lesions, clinical signs and ADWG.

The non-vaccinated treatment group litters are housed in a separate farrowing room than vaccinated treatment groups, this allows for a strict control and prevention to any potential exposure to vaccine. This study evaluates Underline gel for the oral administration of Enterisol *Salmonella* T/C at the sow farm. For this objective, three different treatment groups are used: 1) Non-vaccinated *Salmonella* Challenged Control, 2) Enterisol *Salmonella* T/C gel administration, 3) Enterisol *Salmonella* T/C oral drench administration.

TABLE 7

| Treatment | Treatment Name | Treatment Description | Treatment Dose | Route of Administration |
|---|---|---|---|---|
| 1 | Non-vaccinated, Salmonella challenged control | Non-vaccinated, challenged controls | NA | NA |
| 2 | Enterisol ® Salmonella T/C Underline ® gel administration | Pigs vaccinated with Enterisol ® Salmonella T/C via Underline ® Gel applied on the mat at 14-16 days of age, challenged 28 days later | 120 mL/farrowing crate, approximately 10 mL/piglet in 12 piglet litter; full dose | Oral |
| 3 | Enterisol ® Salmonella T/C oral drench administration | Pigs vaccinated with Enterisol ® Salmonella T/C via oral drench at 14-16 days of age, challenged 28 days later | 1 mL; full dose | Oral |

Sows are *Salmonella* spp. PCR negative. Vaccines are administered to piglets at 14-16 days of age. Piglets are weaned at 21-24 days of age. *Salmonella* challenge (*Typhimurium*) is done at 4 weeks post vaccination (*Salmonella enterica* Serovar *Typhimurium* UK-1, dose of $3.510^{10}$ cfu/mL, 1 mL intranasal (0.5 mL per nostril)). Vaccine efficacy is assessed by a reduction of clinical signs and reduction of intestinal lesions

TABLE 8

Macroscopic lesion evaluation metric for *Salmonella*

| Score | Mesenteric and Ileocecal Lymph Node (one score for each) | Jejunum, Ileum, Cecum, Colon (one score per organ) |
|---|---|---|
| 0 | No gross lesions | No gross lesions |
| 1 | >2x-5x normal size | Mild hyperemia, no abnormal consistency |
| 2 | >5x normal size | Abnormal luminal contents, moderate hyperemia and/or edema, single focal intestinal lesions or ulceration |
| 3 | | Thickened mucosa, multiple or coalescing intestinal lesions and/or ulcerations, adherent mucosal debris |

TABLE 9

Results Gross Lesions Average Score

| Average Score | Treatment 1: Control | Treatment 2: T/C Vx Gel | Treatment 3: T/C Vx Oral Drench | P-value |
|---|---|---|---|---|
| Ileum | — | — | — | — |
| Jejunum | — | — | — | — |
| Caecum | 0.04 ± 0.04 | 0.09 ± 0.09 | 0.04 ± 0.04 | 0.995 |
| Colon | $0.40 ± 0.14^b$ | $0.09 ± 0.09^a$ | $0.04 ± 0.04^a$ | 0.001 |
| Mesenteric LN | 0.25 ± 0.09 | 0.23 ± 0.09 | 0.22 ± 0.09 | 0.96 |
| Ileocecal LN | 0 | 0.05 ± 0.05 | 0.04 ± 0.04 | 0.58 |

Vx = vaccine

TABLE 10

Results Growth (ADWG)

| | Treatment 1: Control | Treatment 2: T/C Vx Gel | Treatment 3: Vx Oral Drench | P-value |
|---|---|---|---|---|
| Number of pigs | 24 | 24 | 24 | — |
| Allocation weight, lbs. | 10.61 | 9.52 | 9.90 | 0.32 |
| Pre-challenge weight, lbs. | 26.88 | 25.73 | 26.65 | 0.69 |
| Necropsy weight, lbs. | 29.34 | 34.05 | 34.99 | 0.08 |
| Allocation to pre-challenge ADG | 0.60 | 0.62 | 10.65 | 0.46 |
| Pre-challenge to necropsy ADG | $0.27^b$ | $0.82^a$ | $0.83^a$ | 0.006 |
| Allocation to necropsy ADG | $0.52^b$ | $0.68^a$ | $0.70^a$ | 0.02 |

Conclusion

Modified live *Salmonella* can be administered by gel compositions for the immunization of pigs. Enterisol® *Salmonella* T/C administered by oral drench or by gel reduces colonic lesions (gross) compared to the non-vaccinated control pigs. Further, there is a significantly greater average daily weight gain compared to the non-vaccinated control pigs.

Example 4

Evaluation of MLV *Lawsonia intracellularis* Efficacy Administered Orally by Gel with a *Lawsonia intracellularis* Seeder Challenge, in Combination with a MLV *Salmonella* Vaccine and Compared to Conventional Water Administration The objective of this study is to evaluate the efficacy of a gel composition for the oral administration of Enterisol® Ileitis (commercially available *Lawsonia intracellularis* vaccine). To validate this approach, vaccine efficacy when administered orally through gel (Underline® gel, commercially available) applied to the farrowing crate mat to pigs at 14-19 days of age will be assessed by experimental challenge by exposure to seeder pigs challenged with a gut homogenate containing virulent *Lawsonia intracellularis* at 12 weeks of age. The second objective of the study is to investigate the mixture of Enterisol® Ileitis with Enterisol *Salmonella* T/C *Salmonella* T/C (commercially available *Salmonella Typhimurium*, *Salmonella Choleraesuis* vaccine) administered by gel (Underline® Gel, commercially available) applied to the farrowing crate mat to pigs at 14-19 days of age followed by experimental challenge by exposure to seeder pigs challenged with a gut homogenate containing virulent *Lawsonia intracellularis* at 12 weeks of age. Gel administration treatments are compared to non-vaccinated challenge control treatment as well as Enterisol® Ileitis vaccination by the conventional oral administration through the water provided at 6 weeks of age. Vaccine efficacy is measured by individual pig differences in weight gain and mortality.

original pens and rubber mats were added for 14 days after being given a challenge dose of approximately $3.7 \times 10^{10}$ *Lawsonia intracellularis* organisms orally per pig. For the challenge of treatment groups, at 48 days post weaning (study day 70), pigs of the four treatments groups were comingled with 6-7 pigs per treatment per final pen location, with treatments groups balanced in each pen. Three seeder pigs were placed in each pen along with rubber mats to promote the challenge of *Lawsonia intracellularis* among pigs. Seeder pig exposure and challenge of treatment groups was done 70 days post-gel vaccination and 42 days post-water vaccination. Mortality was measured after the challenge and comingling of pigs until the final weight study

TABLE 11

Treatment Groups:

| Treatment | Treatment Name | # Reps | Treatment Description | Treatment Dose | Route of Administration |
|---|---|---|---|---|---|
| 1 | Non-vaccinated, *L. intracellularis* challenged control | 540 pigs | Non-vaccinated, challenged controls | NA | NA |
| 2 | Enterisol ® Ileitis gel (14-19 Days of age) | 540 pigs | Pigs vaccinated with Enterisol ® Ileitis via gel applied on the mat at 14-19 days of age, exposed to seeder pigs 70 days later | 120 mL/farrowing crate, approximately 10 mL/piglet assuming 12 piglets/litter; full dose | Oral |
| 3 | Enterisol ® Ileitis water (6 Weeks of Age) | 540 pigs | Pigs vaccinated with Enterisol ® Ileitis via water at 6 weeks of age, exposed to seeder pigs 42 days later | Full dose | Oral |
| 4 | Enterisol ® Ileitis + Enterisol ® *Salmonella* T/C gel (14-19 Days of age) | 540 pigs | Pigs vaccinated with Enterisol ® Ileitis + Enterisol ® *Salmonella* T/C via gel applied on the mat at 14-19 days of age, exposed to seeder pigs 70 days later | 120 mL/farrowing crate, approximately 10 mL/piglet assuming 12 piglets/litter; full dose | Oral |

Prior to challenge, non-vaccinate, water vaccinated groups and pigs to be seeders were housed in a separate room from gel vaccinated treatment groups to prevent exposure to MLV vaccine. Vaccinated treatment groups were separated by multiple pens with Danish biosecurity between groups. All pigs were vaccinated with 3FLEX® post-weaning. For seeder challenge, seeder pigs remained in original pens and rubber mats were added for 14 days after endpoint. Removals or pigs with severe health problems were also measured. All pigs were weighed when allocated to each treatment group at 14 days of age prior to vaccination (study day 0), at comingling of treatments at 84 days of age (study day 70) and at market age of 162 days (study day 148).

TABLE 12

Results of Weight Gain per Treatment Group

| Parameter | Treatment 1: Non-vaccinated, *L. intracellularis* challenged control | Treatment 2: Enterisol ® Ileitis gel (14-19 DOA) | Treatment 3: Enterisol ® Ileitis water (6 WOA) | Treatment 4: Enterisol ® Ileitis + Salmonella T/C gel (14-19 DOA) | P-value | Comingling weight |
|---|---|---|---|---|---|---|
| Allocation weight, lbs. | 10.39 ± 0.09 | 10.39 ± 0.10 | 10.33 ± 0.10 | 10.34 ± 0.09 | 0.96 | — |
| Commingling weight, lbs. | 83.12 ± 0.66$^c$ | 90.13 ± 0.68$^a$ | 83.56 ± 0.69$^{bc}$ | 86.02 ± 0.67$^b$ | <0.0001 | — |
| Final weight, lbs. | 223.42 ± 1.78$^c$ | 248.17 ± 1.80$^a$ | 239.74 ± 1.80$^b$ | 242.85 ± 1.76$^{ab}$ | <0.0001 | — |
| Final weight, lbs | 227.96 ± 1.28$^b$ | 240.09 ± 1.31$^a$ | 243.36 ± 1.30$^a$ | 242.39 ± 1.27$^a$ | <0.0001 | <0.0001 |

TABLE 12-continued

Results of Weight Gain per Treatment Group

| Parameter | Treatment 1: Non-vaccinated, L. intracellularis challenged control | Treatment 2: Enterisol ® Ileitis gel (14-19 DOA) | Treatment 3: Enterisol ® Ileitis water (6 WOA) | Treatment 4: Enterisol ® Ileitis + Salmonella T/C gel (14-19 DOA) | P-value | Commingling weight |
|---|---|---|---|---|---|---|
| ADG (allocation to commingling), lbs./day | $1.04 \pm 0.009^c$ | $1.14 \pm 0.009^a$ | $1.05 \pm 0.009^c$ | $1.08 \pm 0.009^b$ | <0.0001 | — |
| ADG (allocation to final), lbs./day | $1.45 \pm 0.01^c$ | $1.62 \pm 0.01^a$ | $1.56 \pm 0.01^b$ | $1.58 \pm 0.01^{ab}$ | <0.0001 | — |
| ADG (commingling to final), lbs./day | $1.82 \pm 0.02^b$ | $2.05 \pm 0.02^a$ | $2.02 \pm 0.02^a$ | $2.03 \pm 0.02^a$ | <0.0001 | — |
| ADG (commingling to final), lbs./day$^i$ | $1.84 \pm 0.02^b$ | $2.00 \pm 0.02^a$ | $2.04 \pm 0.02^a$ | $2.03 \pm 0.02^a$ | <0.0001 | <0.0001 |

$^i$Commingling weight used as a covariate in the model.
Different superscript letters ($^{a,b,c}$) indicate statistical significance.
ADG = average daily weight gain; DOA = days of age; WOA = weeks of age.

TABLE 13

Results of Mortality and Removals per Treatment Group Post Challenge

| Parameter | Treatment 1: Non-vaccinated, L. intracellularis challenged control | Treatment 2: Enterisol ® Ileitis gel (14-19 DOA) | Treatment 3: Enterisol ® Ileitis water (6 WOA) | Treatment 4: Enterisol ® Ileitis FF + Salmonella T/C gel (14-19 DOA) | P-value |
|---|---|---|---|---|---|
| Removal, % | $1.53 \pm 0.43$ | $0.62 \pm 0.44$ | $1.22 \pm 0.44$ | $0.60 \pm 0.44$ | 0.34 |
| Mortality, % | $5.93 \pm 0.82^b$ | $3.69 \pm 0.85^{ab}$ | $2.88 \pm 0.85^a$ | $2.57 \pm 0.84^a$ | 0.02 |
| Removal and Mortality, % | $7.45 \pm 0.92^b$ | $4.31 \pm 0.95^a$ | $4.11 \pm 0.95^a$ | $3.17 \pm 0.93^a$ | 0.007 |

Different superscript letters ($^a$, $^b$, $^c$) indicate statistical significance.
ADG = average daily weight gain; DOA = days of age; WOA = weeks of age.

Enterisol® Ileitis administered by gel at 14-19 days of age was efficacious and led to significant heavier weights, greater average daily weight gain, and less mortality compared to the non-vaccinated challenged group. This level of efficacy was similar, if not improved, over the conventional water administration of Enterisol® Ileitis. Further, when Enterisol® Ileitis was mixed in the gel with Enterisol Salmonella T/C, the resulting vaccine combination was also efficacious (no interference was observed).

The invention claimed is:

1. An immunogenic gel composition comprising a modified live Lawsonia intracellularis and a modified live Salmonella spp. and a gel composition suitable for application within the barn or housing environment to be accessible to an animal for consumption, wherein the gel composition comprises water, an adhesion enhancing agent, a stabilizer, a flavoring agent, and a colorant, wherein the adhesion enhancing agent is a maltodextrin and/or a cellulose and/or starch and/or a gum.

2. The immunogenic gel composition according to claim 1, wherein said Salmonella spp. is Salmonella Choleraesuis and/or Salmonella Typhimurium and/or wherein the Salmonella spp. is Salmonella enterica subsp. enterica serovar Choleraesuis and/or Salmonella enterica subsp. enterica serovar Typhimurium.

3. The immunogenic gel composition according to claim 1, wherein the immunogenic gel composition comprises about 3.0 to about 9.0 $TCID_{50}$ of the modified live Lawsonia intracellularis per dose and/or, wherein the immunogenic gel composition comprises about $1 \times 10^5$ to about $1 \times 10^{10}$ CFU of the Salmonella spp. per dose.

4. The immunogenic gel composition according to claim 1, wherein the gel composition is viscous or has a viscosity of at least 50 mPa·s or at least 50 cP.

5. The immunogenic gel composition according to claim 1, wherein the gel composition further comprises a pH adjusting agent.

6. The immunogenic gel composition according to claim 1, wherein the gel composition comprises maltodextrins, hemicellulose extract, gum acacia and propylene glycol, or wherein the gel composition comprises maltodextrins, hemicellulose extract, water stabilizing compounds, gum acacia, propylene glycol and artificial coloring.

7. The immunogenic gel composition according to claim 1, wherein the immunogenic gel composition further comprises a veterinary-acceptable carrier and/or, wherein the immunogenic gel composition is vaccine gel composition.

8. A method of immunizing an animal comprising administering to said animal a therapeutically effective amount of an immunogenic gel composition according to any one of claims 1 or 7.

9. A method of treating or preventing clinical signs caused by Lawsonia intracellularis and/or Salmonella spp. in an animal, the method comprising administering to said animal a therapeutically effective amount of an immunogenic gel composition according to claim 7.

10. A method for treating lesions in the intestine in an animal, in comparison to an animal of a non-immunized control group of the same species, comprising administering to said animal an effective amount of the immunogenic gel composition according to claim 7.

11. A method of increasing the average daily weight gain of an animal, in comparison to an animal of a non-immunized control group of the same species, comprising administering to said animal an effective amount of the immunogenic gel composition according to claim 7.

12. The method according to claim 8, wherein the animal is a swine, horse or cattle.

13. The method according to claim 8, wherein the animal is a pig, piglet, sow or swine and/or, wherein the animal is a neonatal pig or a piglet prior to weaning.

14. The method according to claim 8, wherein the immunogenic gel composition is administered to the animal one day of age onwards, three days of age onwards or one week of age onwards or two weeks of age onwards or three weeks of age onwards or, wherein the immunogenic gel composition is administered to the animal between 6 days of age and 20 days of age.

15. The method according to claim 8, wherein the immunogenic gel composition is administered by oral and/or a mucosal route.

16. The method according to claim 8, wherein the method comprises applying the immunogenic gel composition within the barn or housing environment to allow said animal to consume said immunogenic gel composition and/or, wherein the method comprises applying said immunogenic gel composition to the underline of a mother animal or an udder of a mother animal, to a mat within the barn or in a cup or vessel within the barn.

17. The method according to claim 8, wherein the method comprises topically applying the immunogenic gel composition to a mother animal and allowing a postnatal animal or an animal prior to weaning to consume said immunogenic gel composition and/or, wherein the method comprises topically applying said immunogenic gel composition to the underline of a mother animal or, wherein the method comprises topically applying said immunogenic gel composition to at least one teat of a mother animal.

18. The method according to claim 17, wherein the mother animal is a sow and/or the postnatal animal is a postnatal piglet and/or the animal prior to weaning is a piglet prior to weaning.

19. A farrowing mat comprising the gel composition of claim 1.

20. The gel composition of claim 1, wherein the gel composition is suitable for application to the underline of a mother animal or an udder of a mother animal.

21. The gel composition of claim 1, wherein the gel composition is suitable for application to a mat, cup, or other vessel within a housing environment of an animal.

22. An immunogenic gel composition comprising a modified live *Lawsonia intracellularis* and a gel composition suitable for application within the barn or housing environment to be accessible to an animal for consumption, wherein the gel composition comprises water, an adhesion enhancing agent, a stabilizer, a flavoring agent, and a colorant, wherein the adhesion enhancing agent is a maltodextrin and/or a cellulose and/or starch and/or a gum.

23. An immunogenic gel composition comprising a modified live *Salmonella Choleraesuis* and a gel composition suitable for application within the barn or housing environment to be accessible to an animal for consumption, wherein the gel composition comprises water, an adhesion enhancing agent, a stabilizer, a flavoring agent, and a colorant, wherein the adhesion enhancing agent is a maltodextrin and/or a cellulose and/or starch and/or a gum.

\* \* \* \* \*